United States Patent [19]
Leroy et al.

[11] Patent Number: 5,565,192
[45] Date of Patent: Oct. 15, 1996

[54] PROCESS FOR THE PERMANENT-RESHAPING OF HAIR AND COMPOSITION FOR CARRYING IT OUT CONTAINING, IN COMBINATION, AN AMINO- OR AMIDOTHIOL AND AT LEAST ONE INORGANIC BROMIDE

[75] Inventors: Frédéric Leroy, Saint Cloud; Gérard Malle, Villiers sur Morin; Agnès Burande, Villeparisis; Yolanda Duvault, Les Pavillons sous Bois, all of France

[73] Assignee: L'Oreal, Paris, France

[21] Appl. No.: 245,627

[22] Filed: May 18, 1994

[30] Foreign Application Priority Data

May 25, 1993 [FR] France .................. 93 06218

[51] Int. Cl.⁶ .................................................. A61K 7/09
[52] U.S. Cl. ...................... 424/70.5; 424/70.4; 424/70.51
[58] Field of Search .................. 424/70.2, 70.4, 424/70.5, 70.51; 132/205

[56] References Cited

U.S. PATENT DOCUMENTS

| | | | |
|---|---|---|---|
| 3,644,084 | 2/1972 | Hsiung et al. | 8/127.51 |
| 4,192,863 | 3/1980 | Kondo | 424/70.5 |
| 4,659,566 | 4/1987 | Petrow | 424/70.5 |
| 4,749,732 | 6/1988 | Kohl et al. | 524/43 |

FOREIGN PATENT DOCUMENTS

| | | |
|---|---|---|
| 0076444 | 4/1983 | European Pat. Off. . |
| 0295780 | 12/1988 | European Pat. Off. . |
| 0354835 | 2/1990 | European Pat. Off. . |
| 0443356 | 8/1991 | European Pat. Off. . |
| 1530369 | 6/1968 | France . |
| 2470596 | 6/1981 | France . |
| 2472382 | 7/1981 | France . |
| 2495931 | 6/1982 | France . |
| 2535730 | 5/1984 | France . |
| 2598613 | 11/1987 | France . |
| 2654617 | 5/1991 | France . |
| 2663845 | 1/1992 | France . |
| 2676441 | 11/1992 | France . |
| 1959149 | 7/1970 | Germany . |
| 3022049 | 12/1981 | Germany . |
| 63-146808 | 6/1988 | Japan . |
| 2197352 | 5/1988 | United Kingdom . |
| 86/01403 | 3/1986 | WIPO . |
| 91/02538 | 3/1991 | WIPO . |

*Primary Examiner*—John C. Bleutge
*Assistant Examiner*—Robert H. Harrison
*Attorney, Agent, or Firm*—Oliff & Berridge

[57] ABSTRACT

A process for permanently reshaping hair consists of applying an amino compound, an amidothiol compound or a salt of an amino compound or an amidothiol compound as a reducing agent to open the keratin bonds of hair and reforming the bonds using an oxidizing composition or aerial oxygen, wherein prior to or simultaneously with the application of the reducing agent, at least one alkali metal, alkaline-earth metal or ammonium bromide is applied to the hair as a doping agent for the reducing agent. A composition for carrying out the process contains at least one amino compound, amidothiol compound or a salt of an amino compound or an amidothiol compound as a reducing agent, at least one alkali metal, alkaline-earth metal or ammonium bromide as a doping agent for the reducing agent, and a suitable cosmetic vehicle. This process and composition enable improved qualities to be obtained in the permanent reshaping of hair, in particular improved curling.

8 Claims, No Drawings

PROCESS FOR THE PERMANENT-RESHAPING OF HAIR AND COMPOSITION FOR CARRYING IT OUT CONTAINING, IN COMBINATION, AN AMINO- OR AMIDOTHIOL AND AT LEAST ONE INORGANIC BROMIDE

BACKGROUND

The present invention relates to a new process for permanently reshaping hair, consisting in applying an inorganic bromide as a doping agent to hair, prior to or simultaneously with a reduction step using a reducing agent of the amino- or amidothiol type. The present invention also relates to a cosmetic composition containing an amino- or an amidothiol compound and an inorganic bromide for carrying out the first step of permanently reshaping hair.

The technique for permanently reshaping hair consists, in a first stage, of opening the disulphide bonds of keratin (cystins) using a composition containing a reducing agent (reduction step), and then, preferably after rinsing the hair, in reconstituting the disulphide bonds in a second stage by applying an oxidizing composition to the hair under tension (oxidation step, also termed fixing step) so as to give the hair the desired shape. This technique makes it possible to wave, uncurl or straighten hair.

The compositions for carrying out the first stage of permanently reshaping hair generally take the form of lotions, creams, gels or powders diluted in a liquid carrier, and, preferably contain a thiol as a reducing agent.

Among the latter, the products most commonly used are thioglycolic acid, glycerol monothioglycolate and cysteine.

These reducing agents, and in particular thioglycolic acid, which is generally considered to be the reference product for these compositions for permanent-reshaping, reduce the disulphide bonds of keratin effectively.

However, thioglycolic acid does not permit curling of sufficient quality to be obtained when it is used in a sufficiently basic medium, that is to say at a pH above 8.5.

Glycerol monothioglycolate, the pH optimum of which is closer to neutrality, produces inferior curling quality to that obtained with thioglycolic acid.

Although cysteine, which is generally used in the form of L-cysteine base or its hydrochloride, has the advantage of smelling considerably less unpleasant than the above two compounds, its poor reducing power does not enable curling of satisfactory intensity and hold to be obtained. Furthermore, cysteine has to be employed at a very alkaline pH (above 9.0), which influences the degradation of the hairs and increases the irritant power of the composition.

It is therefore desirable to improve the performance of conventional reducing agents while eliminating their drawbacks. The term improvement denotes both improvement in the quality of curling (e.g., the extent, hold, and beauty) obtained using the same amount of product, the ability to use a smaller amount of product and also more satisfactory conditions, such as, for example, at a pH closer to neutrality, making the treatment less degradative to hair.

Various means for improving curling hold and quality have been proposed. Among these, an increase in the exposure time, application of heat and implementation at a higher pH may be mentioned in particular. These means are effective but are unfortunately accompanied by greater degradation of hair.

It has also been proposed to use hair-swelling agents such as formamides and especially urea, alkane diols or alternatively glycol ethers, which promote penetration of the reducing agents into hair and enable some improvement to be obtained in the performance of the reducing agents, but this improvement is very inadequate in relation to amino- and amidothiols and their derivatives such as cysteine.

It has now been found most surprisingly that, when the keratin-reducing agents of the amino- or amidothiol type are combined with an inorganic bromide in well-defined proportions, it is possible to obtain a doping effect on the reducing agent which manifests itself, on the one hand in a large increase in curling hold and intensity, and on the otherhand in the possibility of employing at a neutral pH amino- or amidothiols which normally function at alkaline pH. This improvement in properties is not accompanied by any further degradation of the state of the hair fiber, which is consequently very satisfactory from the cosmetic standpoint.

SUMMARY OF THE INVENTION

The subject of the present invention is hence a process for permanently reshaping hair, consisting of opening the keratin bonds of hair by applying a reducing agent chosen from at least one amino compound, or amidothiol compound or a salt of an amino compound or an amidothiol compound, and then reforming the bonds using an oxidizing composition or by the action of aerial oxygen, wherein prior to or simultaneously with the application of the reducing agent, at least one alkali metal bromide, alkaline-earth metal bromide or ammonium bromide is applied to the hair as a doping agent for the reducing agent.

The amino- or amidothiols which are usable according to the invention may be represented by the formulae (I) and (II) which will be defined below.

Among the alkali metal and alkaline-earth metal bromides which are usable according to the invention, sodium, potassium and calcium bromides may be mentioned in particular.

DESCRIPTION OF PREFERRED EMBODIMENTS

According to a first embodiment of the process according to the invention, the doping agent is applied prior to the reduction step, for 1 to 15 minutes, in the form of a pretreatment composition in which it is present at a concentration of between 1 and 30% by weight relative to the total weight of the composition.

The pretreatment composition is preferably an aqueous solution whose pH is preferably between 4 and 11.

According to a second embodiment of the invention, the doping agent is applied to the hair in combination with the reducing agent in the form of a composition in which the bromide is present at a concentration of between 1 and 30% by weight relative to the total weight of the composition.

According to different variants of the invention, the process for permanently reshaping hair can be a hair waving, a hair uncurling or a hair straightening process.

When the process for permanently reshaping hair is a waving process, wet hair is coiled around rollers from 4 to 20 mm in diameter and the reducing composition is applied. Where appropriate, a pretreatment composition is first applied. In addition, the reducing composition can be applied, where appropriate, as coiling of the hair proceeds.

The reducing composition is allowed to act for 5 to 60 minutes, and preferably for 5 to 30 minutes, at a temperature of between 20° and 55° C., the hair is rinsed copiously, and an oxidizing composition that enables the disulphide bonds of keratin to reform is applied to the coiled hair for an exposure time of 2 to 10 minutes. It is also possible to allow aerial oxygen to act.

The rollers are then removed and the hair is rinsed copiously.

When the process for permanently reshaping hair is a hair uncurling or a hair straightening process, the reducing composition is applied to the hair, and the hair is subjected to mechanical reshaping, for example, smoothing the hair with a broad-toothed comb, with the back of a comb or by hand, which enables it to be fixed in its new shape. Where appropriate the reduction step is preceded by the application of a pretreatment composition.

After an exposure time of 5 to 60 minutes, and especially after 5 to 30 minutes, a further smoothing is carried out, the hair is rinsed carefully, the oxidizing or fixing composition is applied and allowed to act for 2 to 10 minutes and the hair is rinsed copiously.

The subject of the present invention is also a cosmetic composition for permanently reshaping hair containing, in a suitable cosmetic vehicle, at least one amino compound, amidothiol compound or a salt of an amino compound or an amidothiol compound as the one and only reducing agent, and at least one alkali metal, alkaline-earth metal or ammonium bromide as a doping agent for the said agent.

The alkali metal or alkaline-earth metal bromide of the cosmetic composition according to the invention can be, as mentioned above, sodium bromide, potassium bromide and calcium bromide.

The bromide is generally present at a concentration of between 1 and 30% by weight relative to the total weight of the cosmetic composition.

In the cosmetic composition according to the invention, the mole ratio of the doping agent to the reducing agent is preferably between 0.1 and 2.5.

According to the invention, the amino compounds and the amidothiol compounds used as reducing agents in the reducing composition can be represented by the following formulae (I) and (II):

$$HS-A-NR_1R_2 \quad (I)$$

in which:
A represents:
  (a) a divalent radical $-(CH_2)_n-$, n being an integer between 2 and 5,
  (b) the divalent radical $-(CH_2)_2-O-(CH_2)_2-$, or
  (c) a divalent radical

$$-(CH_2)_m-CH-,$$

m being 1 or 2 and $R_3$ being (i) an OH radical or (ii) a radical $OR_4$, $R_4$ represents a linear or branched lower alkyl radical having from 1 to 3 carbon atoms or (iii) a radical $-NR_5R_6$, $R_5$ and $R_6$, which may be identical or different, representing either a hydrogen atom or a linear or branched lower alkyl radical having from 1 to 3 carbon atoms, $R_1$ and $R_2$ represent, independently of one another, a hydrogen atom, a linear or branched lower alkyl radical having from 1 to 4 carbon atoms or radical $-COR_7$, $R_7$ being a linear or branched lower alkyl radical having from 1 to 4 carbon atoms, and $$HS-(CH_2)_p-NR_8R_9 \quad (II)$$

in which:
p is 2 or 3
$R_8$ represents:
  (a) a radical $-CO-(CH_2)_t-OH$, t being an integer between 2 and 5,
  (b) the radical $-CO-(CHOH)_4-CH_2OH$, or
  (c) a radical

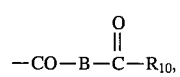

$$-CO-B-C-R_{10},$$

$R_{10}$ represents a hydroxyl radical,
B represents:
  (i) a divalent radical $-(CH_2)_q-$, q being 2 or 3,
  (ii) a divalent radical

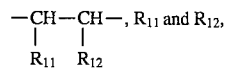

which may be identical or different, represents a linear or branched alkyl radical having from 1 to 4 carbon atoms, or alternatively, $R_{11}$ and $R_{12}$, together with the adjacent carbon atoms, form a cyclohexane ring, or
  (iii) a divalent radical

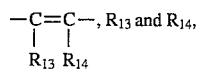

which may be identical or different, represents a hydrogen atom or a linear or branched lower alkyl radical having from 1 to 4 carbon atoms, or alternatively, $R_{13}$ and $R_{14}$, together with the adjacent carbon atoms, form a benzene ring, and $R_9$ represents a hydrogen atom, or $R_9$ and $R_{10}$ taken together form the single bond.

Linear or branched lower alkyl radical having from 1 to 4 carbon atoms should be understood to mean a methyl, ethyl, isopropyl, butyl, isobutyl or 1-methyl-propyl radical.

Among the reducing agents of formulae (I) and (II) above, the following may be mentioned in particular:
cysteine,
methyl cysteinate,
ethyl cysteinate,
N-acetylcysteine,
2-mercaptoethylamine,
3-mercaptopropylamine,
5-mercaptopentylamine,
N-acetylcysteamine,
N-propionylcysteamine,
N-butyrylcysteamine,
N-isobutyrylcysteamine,
N-(2-mercaptoethyl)succinamic acid, and
N-(2-mercaptoethyl) succinimide.

The reducing agent according to the invention as defined above may optionally be used in salt form.

Among cosmetically acceptable salts of the compounds of the formulae (I) and (II), those which are especially preferred are the hydrochlorides, hydrobromides, citrates, or oxalates, lactates and acetates.

The compounds of formulae (I) and (II) are, for the most part, known, and in some instances have been described in Applications FR 90/08,343, FR 89/15,182 and FR 91/06,029 and in European Patent Application 89.402209.

In the reducing compositions according to the invention, the reducing agent as defined above is generally present at a concentration of between 1 and 30%, and preferably between 5 and 20%, by weight relative to the total weight of the reducing composition.

The pH of the reducing compositions according to the invention is preferably between 4 and 11, and more especially between 6 and 10, the pH being obtained using an alkaline agent such as an aqueous ammonia solution, monoethanolamine, diethanolamine, triethanolamine, 1,3-propanediamine, an alkali metal or ammonium carbonate or bicarbonate, an organic carbonate such as guanidine carbonate or an alkali metal hydroxide, or by using an acidifying agent such as, for example, hydrochloric acid, hydrobromic acid, acetic acid, lactic acid, oxalic acid or boric acid, or by using buffers such as, for example, mono- and di-potassium phosphates.

According to a preferred embodiment, the reducing compositions also contain a surfactant of the nonionic anionic, cationic or amphoteric type, and among these there may be mentioned alkyl sulphates, alkylbenzenesulphonates, alkyl ether sulphates, alkylsulphonates, quaternary ammonium salts, alkylbetaines, oxyethylenated alkylphenols, fatty acid alkanolamides and oxyethylenated fatty acid esters, as well as other nonionic surfactants of the hydroxypropyl ether type.

When the reducing compositions contain at least one surfactant, the latter is generally present at a maximum concentration of 30% by weight, but preferably between 0.5 and 10% by weight, relative to the total weight of the reducing composition.

With the object of improving the cosmetic properties of hair, or alternatively, of attenuating or preventing its degradation, the reducing compositions can also contain a treatment agent of a cationic, anionic, nonionic or amphoteric nature.

Among the especially preferred treatment agents, those described in French Patents Nos. 2,598,613 and 2,470,596 may be mentioned in particular. It is also possible to use as treatment agents volatile or non-volatile, linear or cyclic silicones and mixtures thereof, polydimethylsiloxanes, quaternised polyorganosiloxanes such as those described in French Patent Application No. 2,535,730, polyorganosiloxanes containing aminoalkyl groups modified by alkoxycarbonylalkyl groups, such as those described in U.S. Pat. No. 4,749,732, polyorganosiloxanes such as the polydimethylsiloxane/polyoxyalkyl copolymer of the dimethicone copolyol type, a polydimethylsiloxane containing terminal stearoxy groups (stearoxy dimethicone), a polydimethylsiloxane/dialkylammonium acetate copolymer or a polydimethylsiloxane/polyalkylbetaine copolymer which are described in British Patent No. 2,197,352, and polysiloxanes organo-modified by mercapto or mercaptoalkyl groups, such as those described in French Patent No. 1,530,369 and in European Patent Application No. 295,780, as well as silanes such as stearoxytrimethylsilane.

The reducing compositions may also contain other treatment ingredients, for instance cationic polymers such as those used in the compositions of French Patents Nos. 79/32,078 (2,472,382) and 80/26,421 (2,495,931), or alternatively cationic polymers of the ionene type such as those used in the compositions of Luxemburg Patent No. 83703, basic amino acids (such as lysine, arginine) or acidic amino acids (such as glutamic acid, aspartic acid), peptides and their derivatives, protein hydroxates, waxes, swelling and penetrating agents or agents to enable the efficacy of the reducing agent to be enhanced, such as $SiO_2$/PDMS (poly-dimethylsiloxane) mixture, dimethylisosorbitol, urea and its derivatives, pyrrolidone, N-alkylpyrrolidones, thiamorpholinone, alkylene glycol or dialkylene glycol alkyl ethers such as, for example, propylene glycol monomethyl ether, dipropylene glycol monomethyl ether, ethylene glycol monoethyl ether and diethylene glycol monoethyl ether, $C_3$–$C_6$ alkanediols, such as, for example, 1,2-propanediol and 1,2-butanediol and 2-imidazolidinone, as well as other compounds such as fatty alcohols, lanolin derivatives, active ingredients such as pantothenic acid, agents for combating hair loss, anti-dandruff agents, thickeners, suspending agents, sequestering agents, opacifying agents, colorants and sunscreen agents, as well as perfumes and preservatives.

The reducing compositions according to the invention are essentially in aqueous form, in particular in the form of a lotion, thickened or otherwise, a cream or a gel.

The reducing compositions according to the invention may also be of the exothermic type, that is to say, giving rise to some warming on application to the hair, thereby imparting a pleasant sensation to a person undergoing the first stage of permanent-waving or uncurling.

The reducing compositions according to the invention can also contain a solvent such as, for example, ethanol, propanol or isopropanol or alternatively glycerol at a maximum concentration of 20% relative to the total weight of the composition.

The vehicle of the reducing compositions according to the invention is preferably water or an aqueous-alcoholic solution of a lower alcohol such as ethanol, isopropanol or butanol.

When the compositions are intended for hair uncurling or hair straightening, the reducing compositions are preferably in the form of a cream so as to keep the hair as stiff as possible. These creams are produced in the form of "heavy" emulsions, for example based on glyceryl stearate, glycol stearate, self-emulsifying waxes, fatty alcohols, and the like.

It is also possible to use liquids or gels containing thickening agents such as vinylcarboxylic copolymers or polymers which "stick" to the hair and keep it in a smooth position during the exposure time.

The oxidation or oxidizing composition employed in the process for permanently rehaping hair according to the invention is of the type commonly used, and contains hydrogen peroxide, an alkali metal bromate, a persalt, a polythionate or a mixture of alkali metal bromate and persalt as oxidizing agent.

The hydrogen peroxide concentration can vary from 1 to 20 volume percent, and preferably from 1 to 10, the alkali metal bromate concentration from 2 to 12% and that of persalt from 0.1 to 15% by weight relative to the total weight of the oxidizing composition. The pH of the oxidizing composition is generally between 2 and 8, but preferably between 3 and 6. Hydrogen peroxide may be stabilized, for example, with phenacetin, acetanilide or mono- or trisodium phosphates, or with 8-hydroxyquinoline sulphate. Oxidation may be immediate or delayed.

Several examples of the process for permanently reshaping hair as well as of reducing compositions according to the invention will now be given by way of illustration.

EXAMPLE 1

A reducing composition for permanently reshaping hair is prepared according to the invention by mixing the following ingredients:

| | |
|---|---|
| Cysteine | 12.1 g |
| Ammonium bromide | 9.8 g |
| Diethylenetriamine penta-acetic acid pentasodium salt | 0.15 g |
| Perfume q.s. | |
| Aqueous ammonia solution q.s. pH 8.5 | |
| Demineralized water q.s. | 100 g |

This composition is applied to wet hair previously coiled on setting rollers. After the composition has been allowed to act for approximately 15 min, the hair is rinsed copiously with water and the following oxidizing composition is then applied:

| | |
|---|---|
| Hydrogen peroxide | 2 g |
| Sodium stannate | 0.015 g |
| Ammonium lauryl sulphate | 1.4 g |
| Citric acid | 0.5 g |
| Perfume q.s. | |
| Demineralized water q.s. | 100 g |

The oxidizing composition is allowed to act for approximately 5 min, the rollers are then removed and the hair is rinsed copiously with water. After drying under a salon drier, the hair possesses beautiful curls.

In this example, the oxidizing composition may be replaced by the following composition:

| | |
|---|---|
| Sodium bromate | 8 g |
| Triethanolamine q.s. pH 8.0 | |
| Hydrated monosodium phosphate (12 H$_2$O) | 0.3 g |
| Hydrated trisodium phosphate | 0.5 g |
| Cocoamidopropylbetaine sold under the name "Tegobetaine HS" by the company Goldschmidt | 1 g |
| Perfume q.s. | |
| Demineralized water q.s. | 100 g |

EXAMPLES 2 TO 8

According to the same mode of implementation as described above, permanent reshaping of hair was carried out by replacing the reducing composition of Example 1 by one of the following reducing compositions A to H:

Composition A:

| | |
|---|---|
| Cysteine hydrobromide | 22 g |
| Ammonium bromide | 9.8 g |
| Diethylenetriamine penta-acetic acid pentasodium salt | 0.15 g |
| Perfume q.s. | |
| Aqueous ammonia solution q.s. pH 8.5 | |
| Demineralized water q.s. | 100 g |

Composition B:

| | |
|---|---|
| Cysteamine hydrochloride | 11.5 g |
| Ammonium bromide | 9.8 g |
| Laurylamine oxide sold under the name "Aromox DMMCD/W" by the Company Akzo | 2 g |
| Ethylenediaminetetraacetic acid | 0.15 g |
| Perfume q.s. | |
| Monoethanolamine q.s. pH 8.0 | |
| Demineralized water q.s. | 100 g |

Composition C:

| | |
|---|---|
| Cysteine methyl ester | 13.5 g |
| Ammonium bromide | 9.8 g |
| Laurylamine oxide sold under the name "Aromox DMMCD/W" by the company Akzo | 12 g |
| Perfume q.s. | |
| Aqueous ammonia solution (20%) q.s. pH 7.2 | |
| Demineralized water q.s. | 100 g |

The cysteine methyl ester should be added at the time of use.

Composition D:

| | |
|---|---|
| N-Propionylcysteamine | 13.2 g |
| Ammonium bromide | 9.8 g |
| Stearic ester polyoxyethylenated with 8 mol of ethylene oxide, sold under the name "Myrj 45" by the company ICI | 0.85 g |
| Preservative | 0.35 g |
| Perfume q.s. | |
| Aqueous ammonia solution q.s. pH 6.8 | |
| Demineralized water q.s. | 100 g |

Composition E:

| | |
|---|---|
| N-(2-Mercaptoethyl)succinamic acid | 8.8 g |
| Ammonium bromide | 10 g |
| Cysteamine hydrochloride | 6.0 g |
| Laurylamine oxide sold under the name "Aromox DMMCD/W" by the company Akzo | 2.0 g |
| Preservative | 0.15 g |
| Perfume q.s | |
| Monoethanolamine q.s. pH 8.5 | |
| Demineralized water q.s. | 100 g |

Composition F:

| | |
|---|---|
| Cysteine hydrobromide | 22 g |
| Sodium bromide | 10 g |
| Oleocetyldimethylhydroxyethylammonium chloride | 0.3 g |
| Preservative | 0.15 g |
| Perfume q.s. | |
| Aqueous ammonia solution q.s. pH 9.0 | |
| Demineralized water q.s. | 100 g |

Composition G:

| | |
|---|---|
| Cysteine | 12.1 g |
| Potassium bromide | 12 g |
| Diethylenetriamine penta-acetic pentasodium salt | 0.15 g |
| Perfume q.s. | |
| Aqueous ammonia solution q.s. pH 8.5 | |
| Demineralized water q.s. | 100 g |

Composition H:

| | |
|---|---|
| N-Propionylcysteamine | 13.5 g |
| Hydrated calcium bromide | 11.1 g |
| Stearic ester polyoxyethylenated with 8 mol of ethylene oxide, sold under the name "Myrj 45" by the company ICI | 0.9 g |
| Preservative | 0.3 g |
| Perfume q.s. | |
| Aqueous ammonia solution q.s. pH 7.0 | |
| Demineralized water q.s. | 100 g |

EXAMPLE 9

A pretreatment composition is prepared by mixing the following ingredients:

| | |
|---|---|
| Ammonium bromide | 9.8 g |
| Perfume q.s. | |
| Aqueous ammonia solution q.s. pH 9 | |
| Demineralized water q.s. | 100 g |

This composition is applied to wet hair previously coiled on setting rollers. After the composition has been allowed to act for approximately 10 min, the following reducing composition is applied:

| | |
|---|---|
| Cysteine | 12.1 g |
| Diethylenetriamine penta-acetic acid pentasodium salt | 0.15 g |
| Aqueous ammonia solution q.s. pH 9 | |
| Perfume q.s. | |
| Demineralized water q.s. | 100 g |

The composition is allowed to act, the hair is rinsed and the oxidizing composition of Example 1 is applied according to the same mode of implementation as described in that example.

After drying under a salon drier, the hair possesses beautiful curls.

We claim:

1. A process for permanently reshaping hair comprising: applying a first aqueous solution comprising a reducing agent selected from the group consisting of an amino compound, an amidothiol compound or a salt of an amino compound or an amidothiol compound to reduce and open keratin bonds of hair; applying an oxidizing composition to said hair or exposing said hair to aerial oxygen to oxidize and reform said bonds; and applying a second aqueous solution comprising an agent for doping said reducing agent selected from the group consisting of an alkali metal bromide, an alkaline-earth metal bromide and an ammonium bromide to said hair prior to or simultaneously with said first aqueous solution.

2. The process according to claim 1, wherein said alkali metal bromide is selected from the group consisting of sodium bromide, potassium bromide and calcium bromide.

3. The process according claim 1, wherein said first aqueous solution and said second aqueous solution are combined to form a third aqueous solution comprising an admixture of said reducing agent and said doping agent before being applied to said hair, and wherein said doping agent is present in said third aqueous solution at a concentration of 1 to 30 wt %.

4. A method for waving hair comprising the process according to claim 3, wherein said third aqueous solution is applied to hair that has previously been coiled on rollers from 4 to 20 mm in diameter.

5. A method for straightening hair comprising the process according to claim 3, wherein said third aqueous solution is applied to hair prior to subjecting said hair to a mechanical smoothing.

6. A method for waving hair comprising the process according to claim 1, wherein said first aqueous solution is applied to hair that has previously been coiled on rollers from 4 to 20 mm in diameter.

7. A method for straightening hair comprising the process according to claim 1, wherein said first aqueous solution is applied to hair prior to subjecting said hair to a mechanical smoothing.

8. A process for permanently reshaping hair, said process comprising:

(i) applying to said hair a pretreatment composition comprising a doping agent selected from the group consisting of an alkali metal bromide, an alkaline-earth metal bromide and an ammonium bromide, wherein said doping agent is present in said pretreatment composition at a concentration of 1 to 30 wt % based on the total weight of the composition, (ii) applying to said pretreated hair a reducing agent selected from the group consisting of an amino compound, an amidothiol compound or a salt of an amino compound or an amidothiol compound to reduce and open keratin bonds of said hair; and (iii) applying an oxidizing composition to said hair or exposing said hair to aerial oxygen to oxidize and reform said bonds, wherein said pretreatment composition is applied to said hair for approximately 1 to 15 minutes prior to applying said reducing agent.

* * * * *